(12) United States Patent
Wojcik

(10) Patent No.: US 6,572,586 B1
(45) Date of Patent: Jun. 3, 2003

(54) LOW PROFILE INFUSION SET

(75) Inventor: Steven E. Wojcik, Shoreline, WA (US)

(73) Assignee: Animas Corporation, Frazer, PA (US)

( * ) Notice: Subject to any disclaimer, the term of this patent is extended or adjusted under 35 U.S.C. 154(b) by 27 days.

(21) Appl. No.: 09/625,245

(22) Filed: Jul. 25, 2000

(51) Int. Cl.[7] .............................................. A61M 5/178
(52) U.S. Cl. ........................... 604/165.01; 604/164.07; 128/DIG. 6
(58) Field of Search ..................... 604/93.01, 115–116, 604/164.01–164.02, 164.04, 164.07, 165.01–165.02, 165.03, 167.01–167.03, 167.06, 171, 174, 177, 180, 256, 264, 272; 128/DIG. 6, DIG. 26

(56) References Cited

U.S. PATENT DOCUMENTS

| 4,734,092 A | 3/1988 | Millerd |
| 4,755,173 A | 7/1988 | Konopka et al. |
| 4,880,412 A | 11/1989 | Weiss |
| 5,176,662 A | 1/1993 | Bartholomew et al. |
| 5,186,712 A | 2/1993 | Kelso et al. |
| 5,257,980 A | 11/1993 | Van Antwerp et al. |
| 5,522,803 A | 6/1996 | Teissen-Simony |
| 5,545,143 A | 8/1996 | Fischell |
| 5,858,001 A | 1/1999 | Tsals et al. |
| 5,954,643 A | 9/1999 | VanAntwerp et al. |
| 5,980,506 A | 11/1999 | Mathiasen |
| 5,997,501 A | 12/1999 | Gross et al. |
| 6,056,718 A | * | 5/2000 | Funerburk et al. |

* cited by examiner

Primary Examiner—Brian L. Casler
Assistant Examiner—LoAn H. Thanh
(74) Attorney, Agent, or Firm—Akin, Gump, Strauss, Hauer & Feld, L.L.P.

(57) ABSTRACT

An infusion set for administration of fluid to a subcutaneous layer includes a cannula housing adapted for mounting onto a patient's skin and a needle housing for connection to the cannula housing. The needle housing has a pair of flexible sidewalls and a resilient band connected to the sidewalls. The resilient band is lockably engageable with the cannula housing to thereby secure the housings together, and is releasable from the cannula housing when the sidewalls are pressed toward each other to deform the resilient band. A hollow needle extends out of a main body of the needle housing for delivering fluid to the cannula from a fluid source. The walls of the needle housing extend beyond a distal end of the hollow needle to prevent needle contact with contaminated surfaces and inadvertent injury.

24 Claims, 8 Drawing Sheets

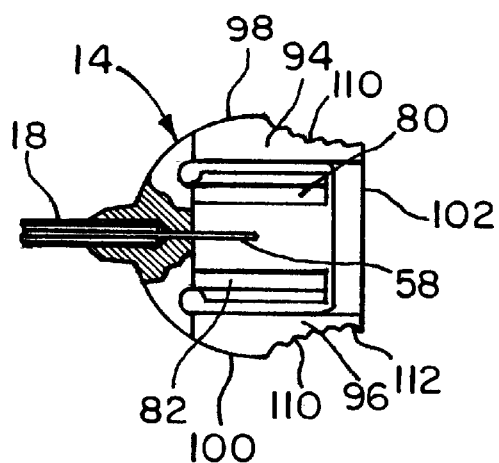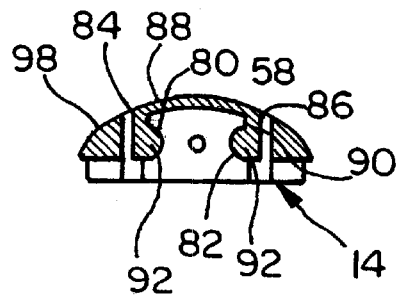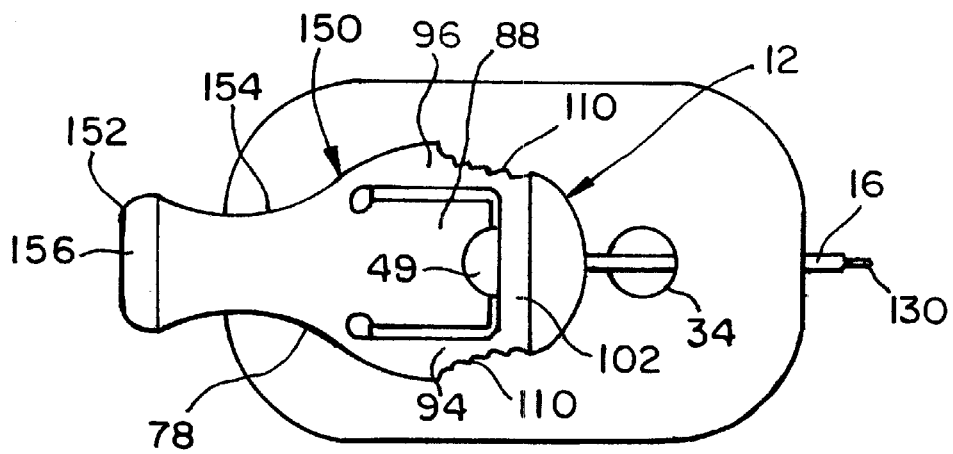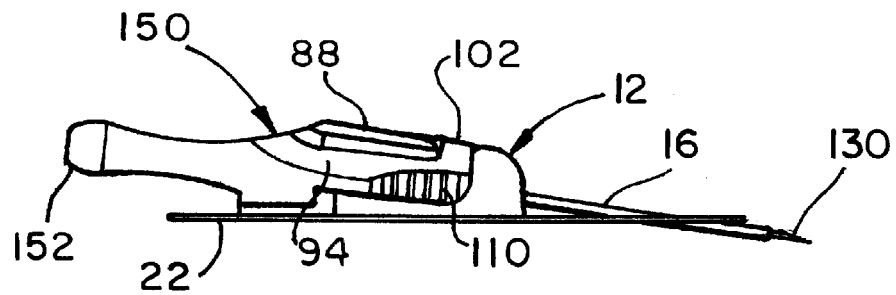

LOW PROFILE INFUSION SET

BACKGROUND OF THE INVENTION

1. Field of the Invention

This invention relates to medical devices, and more particularly to a low profile infusion set for intermittent or continuous subcutaneous administration of medication or other substances beneficial to health.

2. Description of the Related Art

Frequent or continuous subcutaneous injection of medication is often accomplished through the use of an infusion set or injection port which may remain in place for several days. In the case of frequent injections, this reduces the need to constantly puncture the skin and thereby reduce the chance of infection and the formation of scar tissue. For continuous subcutaneous delivery of medication such as commonly used with portable insulin pumps, an infusion set is often used to provide a method of temporarily detaching the pump and fluid line for activities such as dressing or bathing. It is also desirable in this instance to detach the fluid line from the pump as close to the injection site as possible leaving a relatively small component attached to body to minimize the interference during dressing, bathing or other activities.

While devices for this purpose have been proposed, these devices have limitations making them less than ideal in practice. By way of example, U.S. Pat. No. 4,755,173 issued to Konopka et al. on Jul. 5, 1988, discloses a soft cannula subcutaneous injection set that relies on a length of tubing with a separate fluid connector for detachment from the source of medication. No provision is provided for disconnecting the fluid tubing from the injection site. The tubing must either be secured to the body with additional adhesive tape or left to awkwardly hang from the injection site where it has a tendency to snag on clothing.

U.S. Pat. No. 5,545,143 issued to Fischell on Aug. 3, 1996, describes a device for the subcutaneous delivery of medication. This device includes a short tubular extension with a connector to the main body of the device which eliminates the tubing but makes the overall package long and somewhat bulky.

U.S. Pat. No. 5,522,803 issued to Teissen-Simony on Jun. 4, 1996, discloses an infusion set that overcomes some of the problems with the other devices but presents it's own disadvantages. Namely, the infusion needle is not covered for protection against accidental needle sticks or contamination. Also, the cannula housing and needle hub are difficult to align and connect without being directly viewed by the user. This is especially a problem for diabetics with impaired vision. In addition, the guide pins and locking pins of this patent form multiple sharp projecting points which are susceptible to bending or breakage or accidentally poking the user, especially when connecting to injection sites not in the user's direct line of sight.

U.S. Pat. No. 6,056,715 issued to Funderburk et al. on May 2, 2000, discloses an infusion set that is similar to U.S. Pat. No. 5,522,803 and has some of the same problems and disadvantages, particularly in respect to alignment and use of the latch arms and locking fingers which must bend and are susceptible to breaking.

SUMMARY OF THE INVENTION

According to one embodiment of the invention, an infusion set comprises a cannula housing adapted for mounting onto a person's skin and a needle housing for connection to the cannula housing. The cannula housing has a locking element positioned thereon. A cannula is connected to the cannula housing and extends therefrom. The needle housing has at least a first flexible sidewall and a resilient band connected to the sidewall for deformation upon deflection of the sidewall. The resilient band is lockably engageable with the locking element to thereby secure the housings together, and is releasable from the locking element upon deflection of the sidewall to thereby deform the resilient band out of locking engagement with the locking element. A hollow needle extends through the needle housing for delivering fluid to the cannula from a fluid source.

According to a further embodiment of the invention, an infusion set comprises a cannula housing adapted for mounting onto a patient's skin and a needle housing adapted for connection to the cannula housing. A cannula is connected to the cannula housing and extends therefrom. A hollow needle for delivering fluid to the cannula from a fluid source extends from a main body of the needle housing such that a distal end of the hollow needle is spaced from the main body. The needle housing further has first and second sidewalls and an upper wall that extends from the main body beyond the distal end of the hollow needle to thereby prevent inadvertent contact of the hollow needle with contaminated surfaces when the needle housing is separated from the cannula housing.

Other objects and advantages of the invention will become apparent upon review of the following detailed description and appended claims, with reference to the accompanying drawings.

BRIEF DESCRIPTION OF THE DRAWINGS

The preferred embodiments of the present invention will hereinafter be described in conjunction with the appended drawings, wherein like designations denote like elements, and wherein:

FIG. 15 is a bottom plan view of the needle housing;

FIG. 16 is a cross sectional view of the needle housing taken along line 16—16 of FIG. 13;

FIG. 17 is a top plan view of an insertion needle housing connected to the cannula housing;

FIG. 18 is a side elevational view of the insertion needle housing connected to the cannula housing;

It is noted that the drawings are intended to depict only typical embodiments of the invention, and therefore should not be considered as limiting the scope thereof. The invention will now be described with additional detail with particular reference to the drawings.

DETAILED DESCRIPTION OF THE PREFERRED EMBODIMENTS

Figure 1:
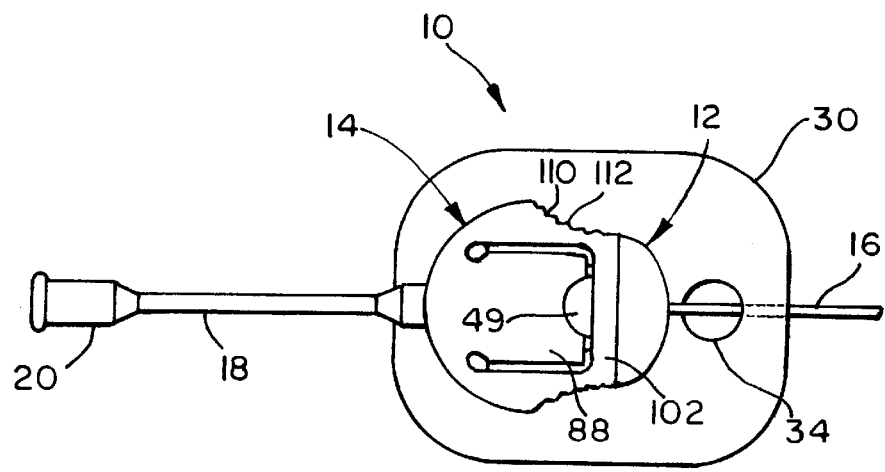
FIG. 1 is a top plan view of the assembled infusion set according to the invention, with a flexible plastic tubing and luer coupling connected at opposite ends of the infusion set.
Figure 2:
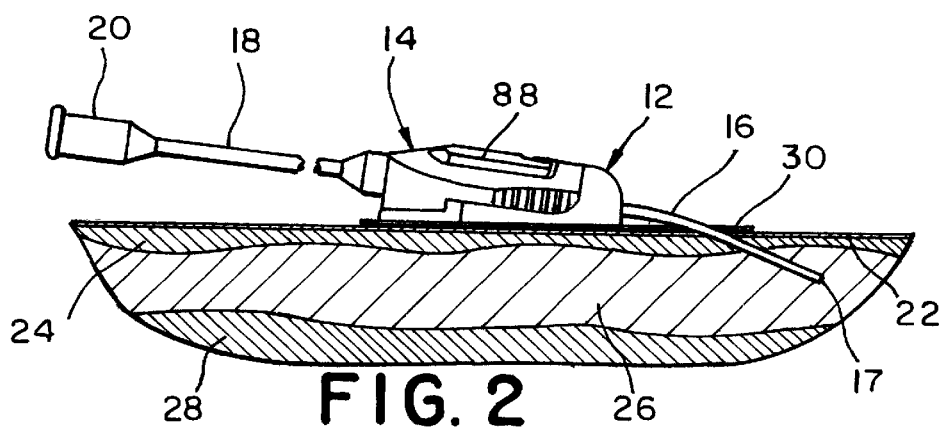
FIG. 2 is a side elevational view of the assembled infusion set in FIG. 1 showing the inserted cannula in a cross section of the skin.

Referring now to the drawings, and to FIGS. 1 and 2 in particular, an infusion set 10 according to the invention includes a cannula housing 12 releasably connected to a needle housing 14. The needle housing 14 may be released from the cannula housing 12, as will be described in greater detail below, for activities such as bathing, dressing, or the like. A flexible cannula 16 is connected to the cannula housing 12. The cannula 16 is adapted to extend through the epidermis layer 22 and dermis layer 24 at an acute angle with respect to the epidermis layer, with an outer free end 17 of the cannula located in the subcutaneous fat layer 26 between the dermis layer 24 and muscle layer 28 for delivering medication or the like to the subcutaneous layer 26. A length of flexible tubing 18 with a fluid connector or Luer fitting 20 is connected to the needle housing 14. The fluid connector 20 is adapted for connection to a source of medication, such as insulin, or other fluids associated with health care for delivery of the fluids to the subcutaneous layer 26 through the housings 12, 14 and the cannula 16.

The particular configuration of the connected housings 12, 14 lends well to reducing the overall size of the infusion set 10 over prior art devices. By way of example, the dimensions may be approximately 16.5 mm wide by 20 mm long by 7 mm high. Cooperating connection members located in the housings (described in greater detail below) afford relatively easy connection and disconnection of the housings, despite the small overall size. It is to be understood that the overall size of the assembled housings may be larger or smaller than the stated dimensions.

A mounting pad 30 is connected to a bottom surface 32 (FIG. 3) of the cannula housing 12. The mounting pad 30 preferably includes an adhesive layer (not shown) for attaching the infusion set 10 to the epidermis layer 22 of a person. The cannula 16 extends through an opening 34 in the mounting pad 30 when the outer free end 17 of the cannula is located in the subcutaneous layer 26.

With reference now to FIGS. 6 through 10, the cannula housing 12 includes a main body portion 38 with series of collinear stepped bores 40, 42 and 44 of increasing diameter formed therein. The bore 40 is the smallest in diameter and extends from a forward end 46 of the cannula housing 12 to the bore 42. The bore 42 in turn extends between the bores 40 and 44. The bore 44 opens at a rearward end 48 of the cannula housing 12. The bores may extend at an angle of about 0° (parallel to the bottom 32 surface) to about 30° with respect to the bottom surface 32, and preferably extend at an angle of approximately 7°. The choice of angle is determined by these considerations. Smaller angles allow the overall height of the assembled infusion set to be minimized for a given bore size, but angling the bore with respect to the bottom 32 minimizes the bending of the cannula and allows the cannula to exit the cannula housing closer to the bottom surface, thereby minimizing the exposure of the cannula above the skin. The preferred angle of 7° provides a reasonable compromise of the desirable properties. Alignment grooves 45, 47 are formed on each side of the cannula housing 12. The alignment grooves 45, 47 preferably extend at the same angle as the bore 40 with respect to the bottom surface 32, for aligning the needle housing 14 with the cannula housing 12 during assembly. A small protrusion 49 and groove 51 are formed on the top surface of the main body to lock the housings 12, 14 together, as will be described in greater detail below. The cannula housing 12 may be injection molded from a plastic, such as polypropylene, polycarbonate, or polyurethane.

Figure 5:
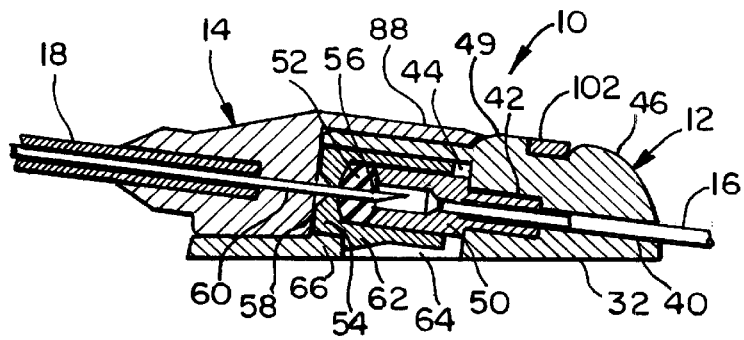
FIG. 5 is a cross sectional view of the assembled infusion set taken along line 5—5 of FIG. 3.
Figure 6:
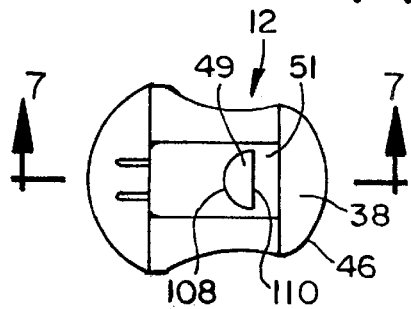
FIG. 6 is a top plan view of a cannula housing that forms part of the infusion set of FIG. 1.
Figure 7:
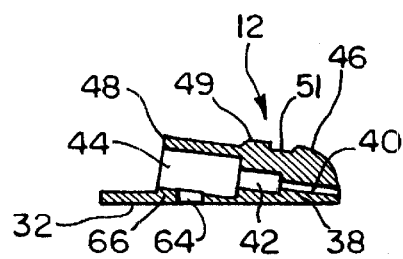
FIG. 7 is a cross sectional view of the cannula housing taken along line 7—7 of FIG. 6.
Figure 8:
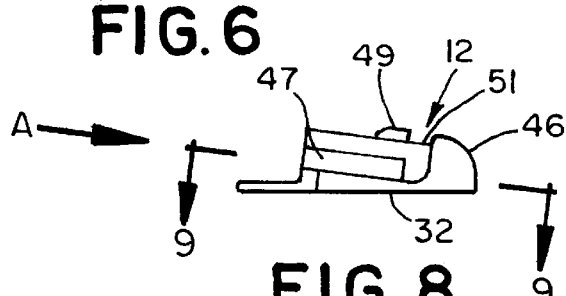
FIG. 8 is a side elevational view of the cannula housing.
Figure 9:
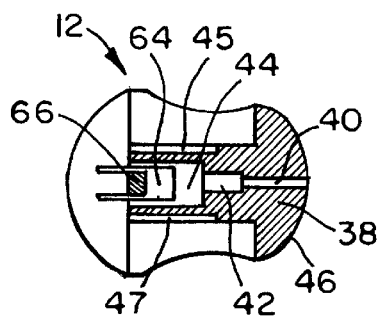
FIG. 9 is a cross sectional view of the cannula housing taken along line 9—9 of FIG. 8.
Figure 10:
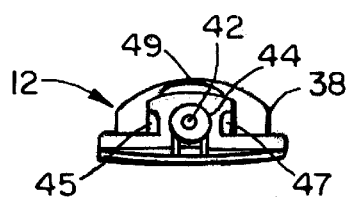
FIG. 10 is a rear elevational view of the cannula housing shown in FIG. 8 in the direction of arrow A.

As shown in FIG. 5, a stepped ferrule 50 is located in the bores 42 and 44. The cannula 16 is fixedly mounted to the ferrule 50 and extends through the bore 40 and outwardly from the forward end 46 a predetermined distance. Preferably, the cannula extends approximately 15 mm beyond the forward end 46 of the cannula housing 12. This length may vary greatly depending on the type of application, the thickness of body layers, and the location of the infusion set when mounted.

A self-sealing elastomeric septum 52 is sandwiched between the ferrule 50 and a septum retainer 54 in the bore 44. The septum 52 has a self-closing aperture 56 that is preferably collinear with a central axis of the bores 40, 42 and 44 to seal the mounted end of the cannula 16 against the ingress of contaminants and the egress of fluids. The septum retainer 54 also includes an aperture 58 in alignment with the aperture 56. A hollow needle 60 extends through the apertures 58 and 56 during use for delivering medication or other substances to the cannula 16 from the fluid source. The septum retainer 54 includes a protrusion 62 that engages a resilient locking tab 66 within an opening 64 at the bottom of the cannula housing 12 to hold the retainer 54, and thus the ferrule 50 and septum 52, within the housing 12. Alternatively, the septum retainer can be bonded, ultrasonically welded, or retained by a snap fit or heat staking in the housing 12.

The ferrule 50 can be molded from a plastic material such as polypropylene or polycarbonate, or formed from a biocompatible metal (e.g. American Society for Testing and Materials (ASTM) grade 304 stainless steel). The elastomer septum can be constructed of a medical grade silicone rubber. The cannula retainer can also be molded from a plastic material such as polypropylene or polycarbonate.

During assembly, the cannula 16, ferrule 50, septum 52, and septum retainer 54 are inserted into the bore 44 of the cannula housing 12 with the distal end 17 of the cannula extending out of the forward end 46 of the housing. An inner connection end of the cannula is preferably connected to the ferrule, but may alternatively be directly connected to cannula housing 12.

With particular reference now to FIGS. 11 through 16, the needle housing 14 includes a main body portion 70 with a pair of collinear stepped bores 72, 74 of increasing diameter formed therein. The bore 72 is the smallest in diameter and extends from a forward end 76 of the main body 70 to the bore 74. The bore 74 in turn extends between the bore 72 and the rearward end 78 of the needle housing 14. The bores 72, 74 may extend at an angle of about 0° (parallel to the bottom surface 32) to about 30° with respect to the bottom surface 32 of the cannula housing 12 when assembled, and preferably extend at an angle of approximately 7°. The needle 58 extends through the bore 72 with an outer end of the needle extending forwardly of the bore 72. Likewise, the tubing 18 is positioned in the bore 74 and extends outwardly from the rearward end 78 of the needle housing 14. An upper wall 88 is formed with the main body portion 70 and extends forwardly therefrom. Guide rails 80 and 82 protrude generally downwardly from opposite sides 84 and 86, respectively, of the upper wall 88. Each guide rail includes a relatively straight portion 90 that terminates in a semi-cylindrical portion 92. The semi-cylindrical portions 92 are adapted to slidably engage the to alignment grooves 45, 47 of the cannula housing 12 during assembly for aligning the needle housing 14 with the cannula housing 12. The needle housing is preferably molded of a flexible, resilient plastic material such as polypropylene, polycarbonate, or polyurethane.

In an alternative embodiment, the cross sectional shape of the guide rails and alignment grooves can be square, rectangular, triangular, rounded, or any other suitable shape. Clearance between the guide rails and alignment grooves is preferably on the order of about 0.05 mm to accurately locate the needle 58 with the septum 52 but still enable the needle housing 14 to slide freely on the cannula housing 12.

Resilient sidewalls 94 and 96 are formed at opposite sides 98 and 100, respectively, of the main body portion 70. The resilient sidewalls 94 and 96 extend forwardly of the forward end 76 and generally parallel to the sides 84 and 86, respectively, of the upper wall 88. The forward ends of the sidewalls 94, 96 are joined together by a resilient, arcuate locking band 102. The band 102 is curved generally upwardly and is adapted to seat within the groove 51 when the housings 12 and 14 are assembled to thereby lock the housings together. A slot 104 is located between the upper wall 88, the resilient sidewalls 94, 96 and the resilient band 102. The sidewalls 94 and 96 flex inwardly toward each other but are preferably relatively stiff in bending in all other planes. In order to reduce the overall length of the assembled housings, a notch 106 is formed in the upper wall 88 to provide clearance for the protrusion 49.

The upper wall 88 has a sufficient length and the sidewalls 94, 96 and guide rails 80, 82 have a sufficient height to extend beyond the end of the needle 58. In this manner, the needle 58 is well shielded to prevent contact with contaminated surfaces and accidental needle punctures when the needle housing 14 is disconnected from the cannula housing 12.

Figure 3:
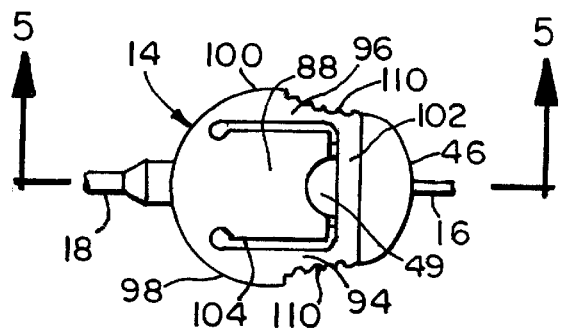
FIG. 3 is a top plan view of the assembled infusion set absent a mounting pad.
Figure 4:
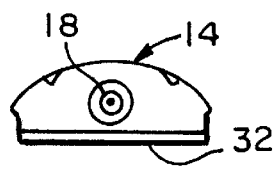
FIG. 4 is rear elevational view of the assembled infusion set of FIG. 3, absent the luer coupling.

With reference now to FIGS. 1, 3 and 5, during connection of the needle housing 14 with the cannula housing 12, the guide rails 80, 82 of the needle housing engage the alignment grooves 45, 47, respectively, of the cannula housing to pre-align the needle 58 with the aperture 56 of the septum 52 before the septum is penetrated by the needle. As the needle housing slides onto the cannula housing, the resilient band 102 of the needle housing deflects upwardly over the protrusion 49 of the cannula housing, causing deflection of the sidewalls 94, 96 toward each other. Once the band 102 passes over the protrusion 49, it snaps back to its undeflected position in the groove 51 to thereby lock the housings together. This also results in an audible click or snapping sound which reassures the user that a secure connection has been made.

In order to disconnect the needle housing 14 from the cannula housing 12, the sidewalls 94, 96 are squeezed toward each other with finger pressure to thereby deflect the resilient band 102 above the protrusion 49 on the cannula housing. This allows the needle housing to slide freely off the cannula housing.

The protrusion 49 on the cannula housing 12 preferably has a smooth, rounded rear side 108 (FIG. 6) that blends with the top surface of the cannula housing and a relatively flat forward side 110 nearest the cannula 16. When viewed from above, the base of the protrusion is semi-circular with the forward side adjacent the resilient band 102 to thereby hold the band in the groove 51. The rounded shape of rear side 108 allows the band 102 to be pushed and flexed over the protrusion 49 without squeezing the sidewalls 94, 96 together. Depending on the amount of sidewall movement desired, the height of the protrusion 49 above the top surface of the cannula housing can be varied in order to vary the amount of band deflection. The height of the protrusion 49 may be approximately equal to the band thickness. In one exemplary embodiment, the band thickness and the protrusion height is about 0.75 mm to thereby securely lock the housings and permit easy release of the housings when desired.

While it is possible to use a single flexible sidewall connected through the resilient gee band to a fixed sidewall or other member, the dual flexible sidewalls 94, 96 provide a degree of safety against accidental release. Since both sidewalls 94, 96 must be simultaneously squeezed toward each other, the needle housing 14 will not be released if one sidewall is inadvertently pressed, since both sidewalls would deflect in the same direction and fail to deflect the resilient band 102.

Figure 11:
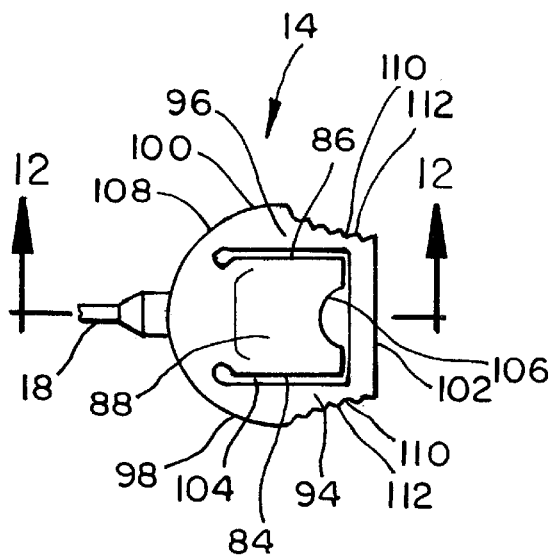
FIG. 11 is a top plan view of a needle housing that forms part of the infusion set of FIG. 1.
Figure 12:
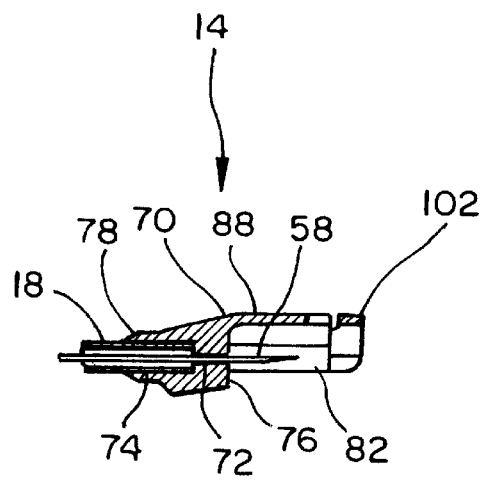
FIG. 12 is a cross sectional view of the needle housing taken along line 12—12 of FIG. 11.
Figure 13:
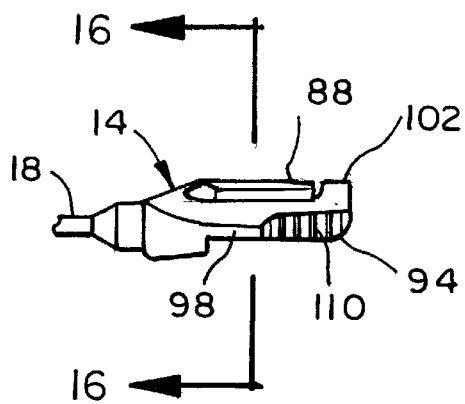
FIG. 13 is a side elevational view of the needle housing.
Figure 14:
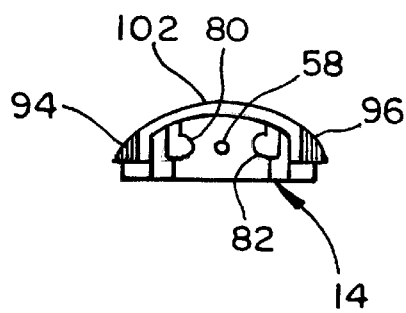
FIG. 14 is a front elevational view of the needle housing.

As shown in FIG. 11, disconnection of the needle housing 14 from the cannula housing 12 can be facilitated by arranging the forward ends of the flexible side members 94, 96 to be narrower in width (in the plane of the skin) than the than the rearward end 108 of the needle housing. This could be achieved in a number of ways such as making the overall shape of the housing tapered towards the resilient band 102 so that the user would grip the narrower end and pull towards the wider end of the needle housing. According to a preferred embodiment, curved finger recesses 110 are formed on the flexible members at the forward end of the needle housing adjacent the resilient band 102 to thereby provide a natural location for finger and thumb placement when disconnecting the needle housing. The grip may also be enhanced by providing small serrations 112 in the curved recesses.

Referring again to FIG. 5, while the cannula 16 can be molded as an integral part of the cannula housing, fabricating the cannula separate from the cannula housing is preferred since the material used for each component can be optimized. The cannula 16 is preferably a thin walled, bio-compatible tube constructed of Teflon, such as polytetrafluorethylene, or other suitable material. Where Teflon tubing is used, it may be necessary to pretreat the attachment end of the cannula prior to adhesively bonding the cannula to the cannula housing 12. Alternatively, the cannula can be bonded to the ferrule 50. Although the size of the cannula can vary, an outside diameter of approximately 0.6 mm is preferred.

Figure 19A:
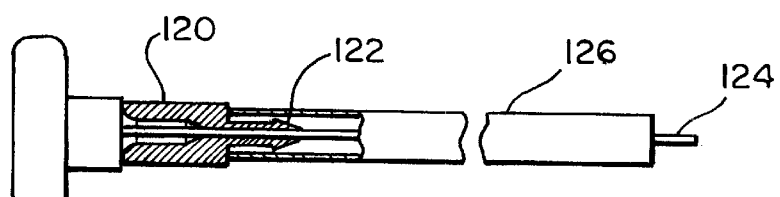
FIGS. 19A and 19B are side elevational views of a cannula and ferrule associated with the cannula housing and their method of assembly according to a further embodiment of the invention.
Figure 19B:
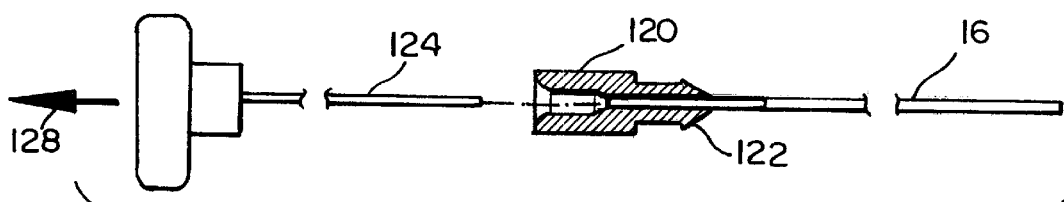
Figure 20:
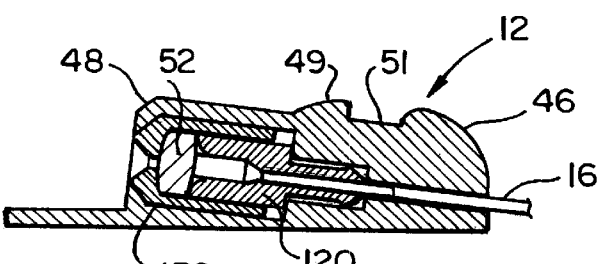
FIG. 20 is a cross sectional view similar to FIG. 5 and illustrating a further embodiment of the invention for retaining the cannula and a septum associated with the cannula in the infusion set.

With particular reference to FIGS. 19A, 19B and 20, a further embodiment for connecting the cannula 16 to the cannula housing 12 is shown, wherein like parts in the previous embodiment are represented by like numerals. In this embodiment, a ferrule 120 includes a barb 122 for receiving a heat-shrink tubing 126, which is preferably constructed of Teflon. A removable metal mandrel 124 that is substantially equivalent in diameter to an insertion needle 130 (FIG. 17) is inserted through the ferrule 120 and heat-shrink tubing 126. Heat is then applied to the tubing 126, causing it to shrink and deform around the barb 122 of the ferrule and the mandrel 124. Due to the relatively low coefficient of friction associated with the Teflon material, the mandrel 124 is easily removed in a direction denoted by arrow 128 in FIG. 19B. In this manner, the heat-shrink tubing 126 forms the cannula 16, which is tightly held on the ferrule 120. The ferrule and attached cannula 16 can then be installed in the cannula housing 12 together with the septum 52 and septum retainer 54. As shown in FIG. 20, the retainer 54 is cylindrical along a substantial portion of its length, and includes a frustro-conical end portion 132 that faces rearwardly with respect to the cannula housing 12. The rearward end 48 of the cannula housing 12 is then deformed over the frustro-conical end portion 132, such as by heat staking, in order to permanently mount the cannula, ferrule, septum, and septum retainer in the cannula housing.

Figure 23A:
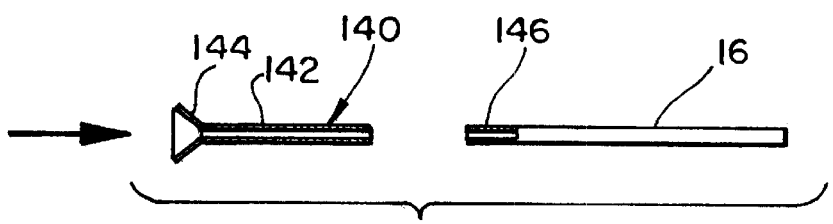
FIGS. 23A and 23B and are side elevational views of a ferrule according to a further embodiment of the invention and the manner in which the cannula is joined to the ferrule.
Figure 23B:
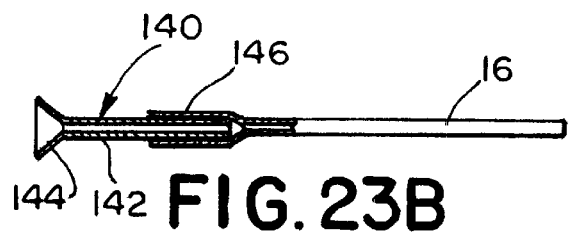
Figure 24:
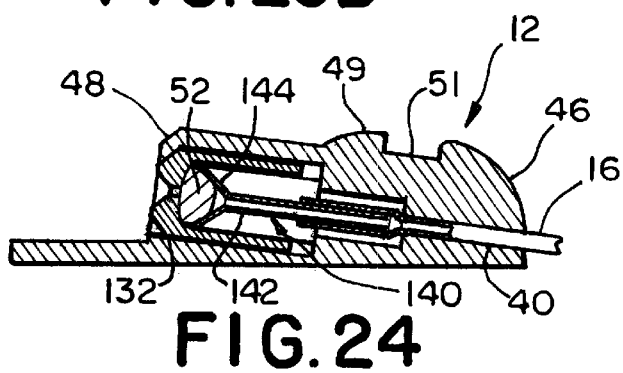
FIG. 24 is a cross sectional view similar to FIG. 20 and illustrating the cannula and ferrule of FIGS. 23A and 23B mounted in the infusion set.
Figure 25:
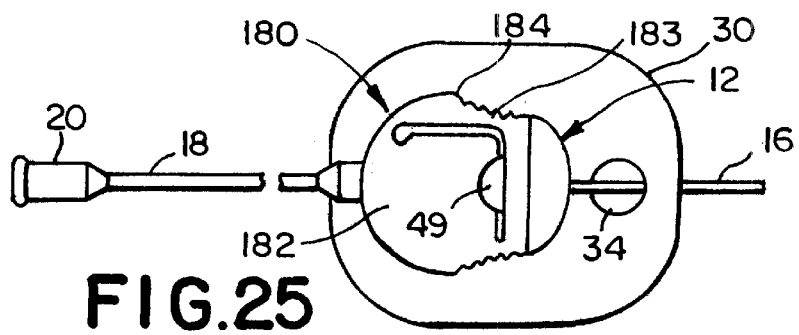
FIG. 25 is a top plan view of the assembled infusion set similar to FIG. 1 and illustrating a further embodiment of the invention.
Figure 26:
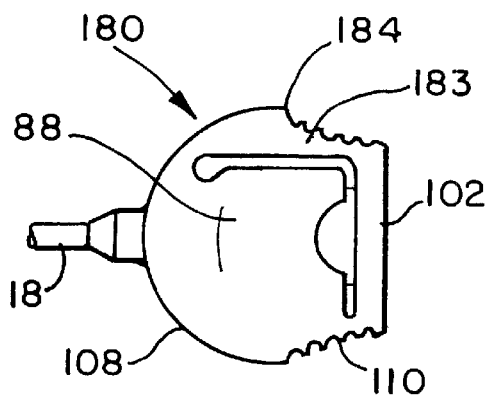
FIG. 26 is a top plan view of a needle housing that forms a part of the infusion set of FIG. 25.
Figure 27:
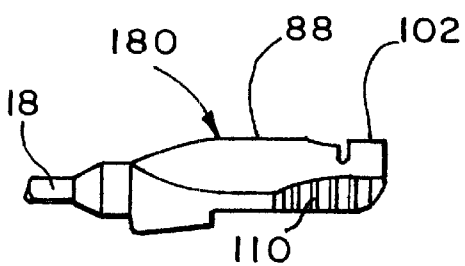
FIG. 27 is a side elevational view of the needle housing.
Figure 28:
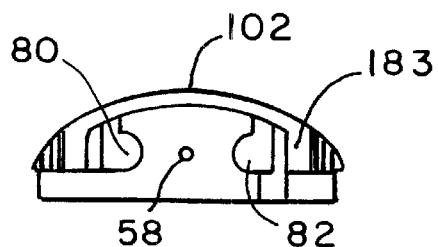
FIG. 28 is a front elevational view of the needle housing.

Referring now to FIGS. 23A, 23B and 24, a further embodiment for connecting the cannula 16 to the cannula housing 12 is shown, wherein like parts in the previous embodiments are represented by like numerals. In this embodiment, a ferrule 140 is provided with a hollow shaft portion 142 and a hollow conical portion 144 connected to one end of the shaft portion. The inner diameter of the shaft portion is preferably slightly greater than the outer diameter of the insertion needle 130 (FIG. 17) so that the insertion needle is free to slide within the ferrule 140. In order to install the cannula 16 on the ferrule 140, an attachment end 146 of the cannula 16 is heated to soften the attachment end. The shaft portion 142 is then inserted into the attachment end 146, thereby expanding the diameter of the attachment end and creating a tight seal between the cannula 16 and the ferrule 140. As shown in FIG. 24, the septum 52 acts as a biasing member to press the expanded attachment end 146 against the opening of the bore 40 to thereby form a compression seal.

With reference now to FIGS. 17 and 18, an insertion needle housing 150 for use with the cannula housing 12 is illustrated. The insertion needle housing 15 generally resembles the needle housing 14, with the exception that a handle 152 is formed at the rearward end 78 of the housing, and an insertion needle 130 is provided. The needles used in both the needle housing and insertion needle assembly are preferably 27 gauge stainless steel tubing (ASTM grade 304) beveled at one end to create a sharp angled edge. As shown, the handle is generally hour-glass in shape with a gripping surface 154 located between the rearward end 78 and an enlarged head 156. The hourglass shape of the handle 152 improves the grip during installation of the cannula 16 in the skin and mounting of the cannula housing 12 on the skin.

When the insertion needle assembly is connected to the cannula housing assembly with the same guide rail, sidewall and band configuration as the needle housing 12, the end of the insertion needle 130 extends beyond the outer free end of the cannula 16, which may be about 2 or 3 mm. The handle 152 on the insertion needle housing 150 allows the combined assembly of the insertion needle housing 150 and cannula housing 12 to be grasped with one hand while pinching a fold of skin with the other hand. The combined assembly can then be pressed into the pinched skin until the needle 130 punctures the skin along with the cannula. The mounting pad 30 can then be attached to the surface of the skin. This may be accomplished by removing a protective backing layer (not shown) to expose an adhesive layer on a lower surface of the mounting pad. Once the cannula housing 12 and cannula 16 are properly mounted, the insertion needle housing 150 is removed by pinching the resilient sidewalls 94, 96 to release the band 102 from the groove 51 in the cannula housing 12. The needle housing 14 can then be attached to the cannula housing 12 to begin delivery of the medication or other fluid.

Figure 21:
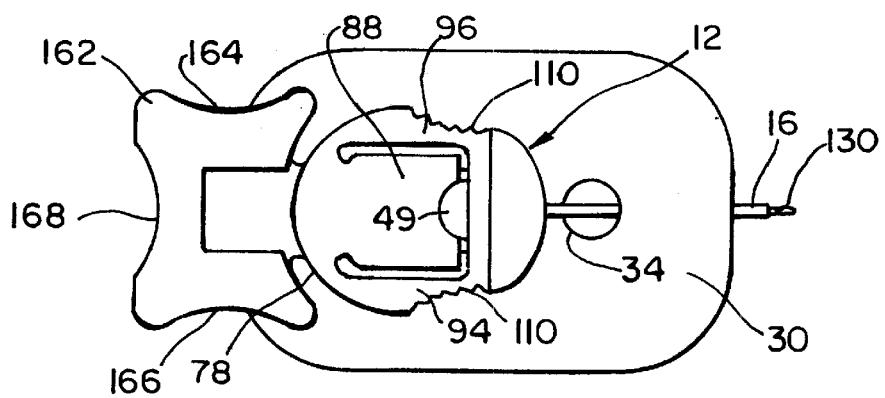
FIG. 21 is a top plan view of an insertion needle housing according to a further embodiment of the invention connected to the cannula housing.
Figure 22:
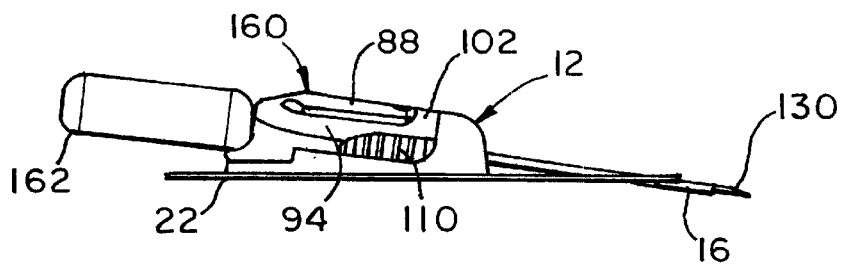
FIG. 22 is a side elevational view of the insertion needle housing and cannula housing of FIG. 21.

With reference now to FIGS. 21 and 22, an insertion needle housing 160 according to a further embodiment of the invention for use with the cannula housing 12 is illustrated, wherein like parts in the previous embodiments are represented by like numerals. The insertion needle housing 160 is substantially similar to the insertion needle housing 150, with the exception that a handle 162 has a different configuration than the handle 152. As shown, the handle 162 is generally rectangular and includes first, second and third gripping surfaces 164, 166, and 168, respectively. The gripping surfaces are preferably curved generally inwardly to thereby prevent or reduce inadvertent slipping during mounting of the cannula housing 12 and cannula 16.

With reference now to FIGS. 25, 26, 27 and 28, an infusion set 180 according to a further embodiment of the invention is illustrated, wherein like parts in the previous embodiments are represented by like numerals. The insertion needle housing 182 is substantially similar to the insertion needle housing 14, with the exception that the housing has only one resilient sidewall 183 formed at one side 184 of the main body portion 70. Except for the use of only one resilient sidewall, the needle housing 182 is structurally the same as the needle housing 14, or may, if desired, the needle housing 14 may have the structure of the other alternative embodiments described herein. The forward end of resilient sidewall 183 is joined to curved band 102 which is adapted to seat within a groove in the cannula housing 12.

The needle housing 182 is joined to the cannula housing 12. During connection of the needle housing 180 with the cannula housing 12, the guide rails 80, 82 of the needle housing engage the alignment grooves 45, 47, respectively, of the cannula housing to pre-align a needle (not shown) with the aperture of the septum before the septum is penetrated by the needle. As the needle housing slides into the cannula housing, the resilient band 102 of the needle housing deflects upwardly over the protrusion 49 of the cannula housing, causing deflection of the single sidewall 183 laterally inward. Once the band 102 passes over the protrusion 49, it snaps back to its undeflected position in the groove to thereby lock the housings together. This also results in an audible click or snapping sound which reassures the user that a secure connection has been made.

To disconnect the needle housing 180 from the cannula housing 12, the one sidewall 183 is squeezed laterally inward with finger pressure to thereby deflect the resilient band 102 above the protrusion on the cannula housing. This allows the needle housing to slide freely off the cannula housing.

Figure 29:
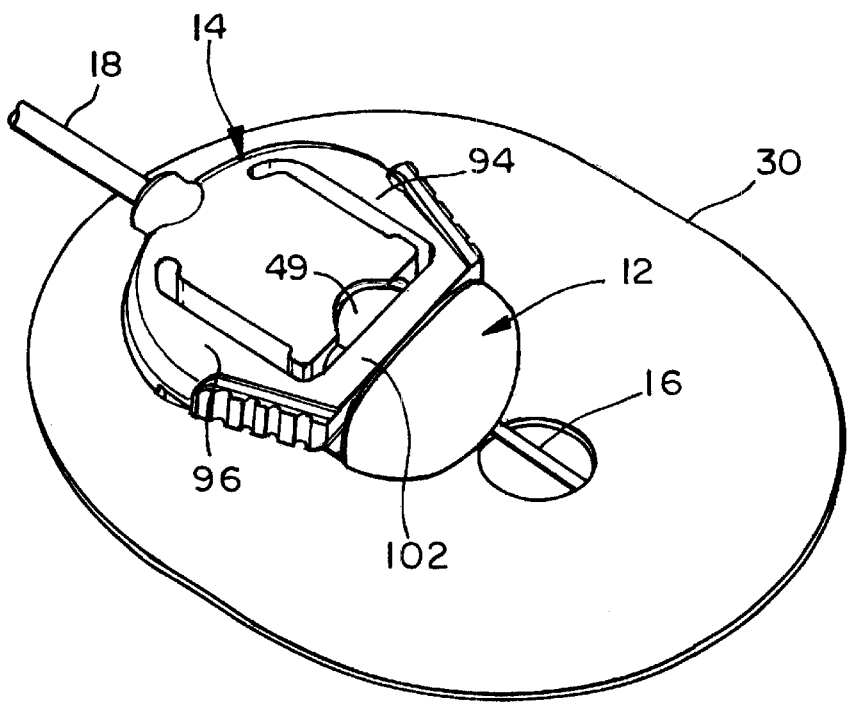
FIG. 29 is a perspective view of an assembled infusion set.
Figure 30:
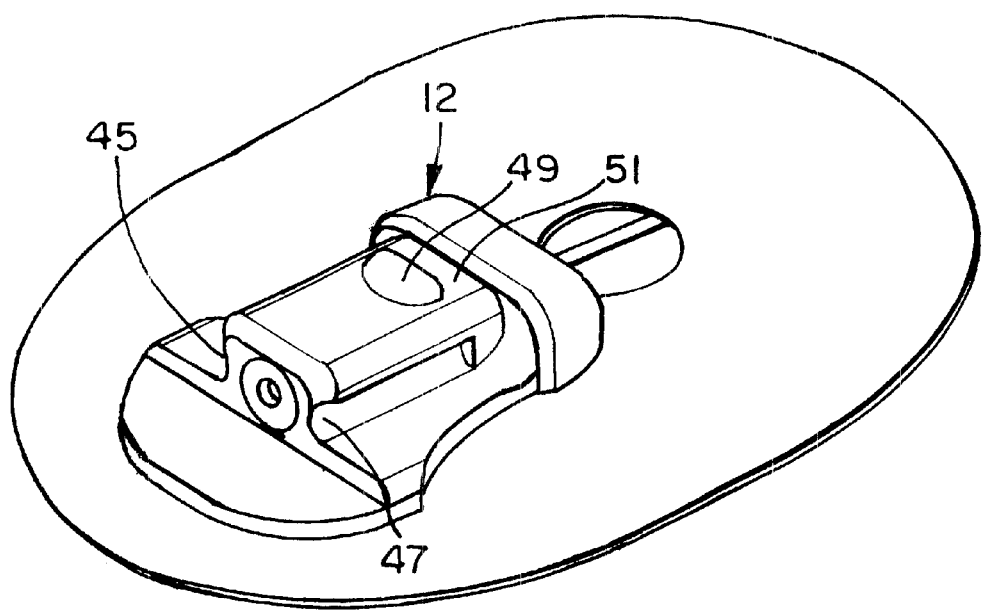
FIG. 30 is a perspective view of the cannula housing with the needle housing removed.

Finally, for ease of further understanding the invention, FIG. 29 is a perspective view 10 of the assembled infusion set illustrated in FIGS. 1 through 16. FIG. 30 is a perspective of the cannula housing with the needle housing removed to better show how the parts fit together.

Figure 31:
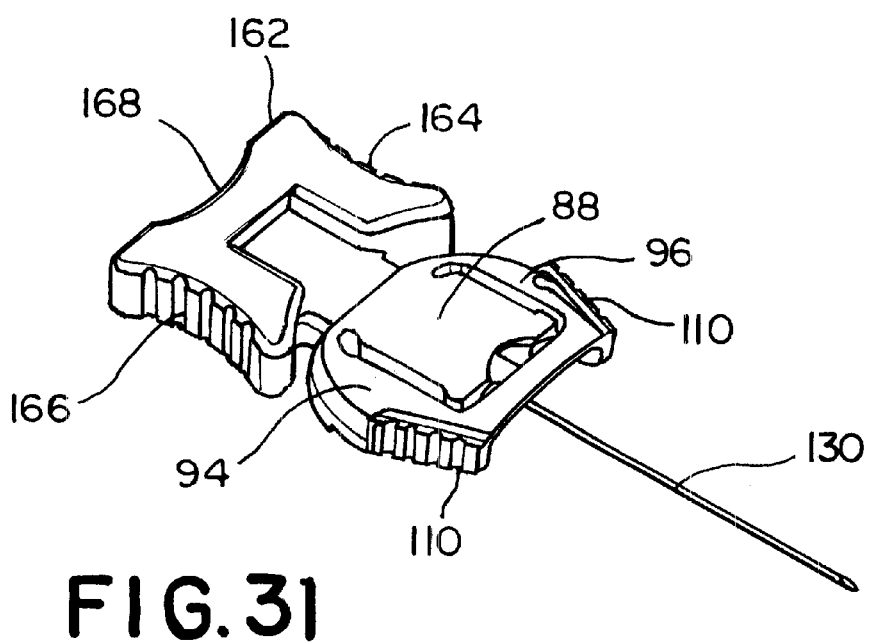
FIG. 31 is a prospective view of a needle housing of a different embodiment of the invention removed from the cannula housing.

FIG. 31 is a perspective view of the needle housing shown in FIGS. 20 and 21, again, to better show the operability of the device.

While the invention has been taught with specific reference to the above-described embodiments, those skilled in the art will recognize that changes can be made in form and detail without departing from the spirit and the scope of the invention. Thus, the described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. An infusion set, comprising:
a cannula housing adapted for mounting onto a person's skin, said cannula housing having a locking element positioned thereon;
the cannula housing being adapted for connection to a cannula extending therefrom;
a needle housing adapted for connection to the cannula housing, the needle housing having at least a first flexible sidewall and a resilient band connected to the sidewall for deformation upon deflection of the sidewall, the resilient band being lockably engageable with the locking element to thereby secure the housings together, the resilient band being releasable from the locking element upon deflection of the sidewall to thereby deform the resilient band out of locking engagement with the locking element; and
a hollow needle connected to the needle housing for delivering fluid to the cannula from a fluid source.

2. An infusion set according to claim 1, wherein the needle housing further comprises a second sidewall spaced from the first sidewall, with the resilient band extending between and connected to the first and second sidewalls, such that depression of the first and second side walls toward each other causes the resilient band to deform out of locking engagement with the locking element to thereby disconnect the housings.

3. An infusion set according to claim 2, wherein the first and second sidewalls taper toward the resilient band.

4. An infusion set according to claim 1, wherein the locking element comprises a protrusion formed on an upper surface of the cannula housing for engaging the resilient band.

5. An infusion set according to claim 4, wherein the locking element further comprises a groove formed in the upper surface of the cannula housing adjacent the protrusion, the groove being sized to receive the resilient band.

6. An infusion set according to claim 1, and further comprising:
a ferrule mounted in the cannula housing such that a cannula can be connected to a forward end of the ferrule; and
a septum connected at a rearward end of the ferrule to seal the ferrule against ingress and egress of fluid when the housings are disconnected, the hollow needle extending through the septum and into the ferrule when the housings are connected.

7. An infusion set according to claim 6, and further comprising at least one alignment groove formed on one of the housings and at least one guide rail formed on the other housing, the alignment groove and guide rail being engageable during sliding movement of the housings to thereby center the hollow needle relative to the septum and ferrule during connection of the housings.

8. An infusion set according to claim 6, wherein a barb is formed on the forward end of the ferrule and a connection end of the cannula is in sealing engagement with the barb.

9. An infusion set according to claim 8, wherein the cannula housing includes a bore through which a cannula can extend.

10. An infusion set according to claim 9, wherein the septum is constructed of a resilient material that biases the connection end of the cannula into sealing engagement with an edge of the bore.

11. An infusion set according to claim 6, and further comprising a septum retainer mounted between the cannula housing and the septum.

12. An infusion set, comprising:
a cannula housing adapted for mounting onto a person's skin, said cannula housing having a locking element positioned thereon;
the cannula housing being adapted for connection to a cannula extending a therefrom;
a needle housing adapted for connection to the cannula housing, the needle housing having at least a first flexible sidewall and a resilient band connected to the sidewall for deformation upon deflection of the sidewall, the resilient band being lockably engageable with the locking element to thereby secure the housings together, the resilient band being releasable from the locking element upon deflection of the sidewall to thereby deform the resilient band out of locking engagement with the locking element; and
a hollow needle connected to the needle housing for delivering fluid to the cannula from a fluid source;
wherein the resilient sidewall extends beyond a distal end of the hollow needle to thereby prevent the needle from touching a contaminated surface.

13. An infusion set, comprising:
a cannula housing adapted for mounting onto a person's skin, said cannula housing having a locking element positioned thereon;

the cannula housing being adapted for connection to a cannula extending therefrom;

a needle housing adapted for connection to the cannula housing, the needle housing having at least a first flexible sidewall and a resilient band connected to the sidewall for deformation upon deflection of the sidewall, the resilient band being lockably engageable with the locking element to thereby secure the housings together, the resilient band being releasable from the locking element upon deflection of the sidewall to thereby deform the resilient band out of locking engagement with the locking element; and a hollow needle connected to the needle housing for delivering fluid to the cannula from a fluid source;

wherein the resilient sidewall extends beyond a distal end of the hollow needle to thereby prevent the needle from touching a contaminated surface; and wherein the needle housing further comprises an upper wall that extends beyond a distal end of the hollow needle.

14. An infusion set, comprising:

a cannula housing adapted for mounting onto a patient's skin;

a hollow needle for delivering fluid to the cannula from a fluid source; and a needle housing adapted for connection to the cannula housing, the needle housing having a main body for holding the hollow needle such that a distal end of the hollow needle extends beyond the main body, the needle housing further having first and second sidewalls and an upper wall extending from the main body beyond a distal end of the hollow needle to thereby prevent inadvertent contact of the hollow needle with contaminated surfaces when the needle housing is separated from the cannula housing.

15. An infusion set according to claim 14, wherein the sidewalls are flexible, and further comprising a resilient band extending between and connected to the sidewalls for deformation upon deflection of the sidewalls toward each other, the resilient band being lockably engageable with the cannula housing to thereby secure the housings together, the resilient band being releasable from the cannula housing upon deflection of the sidewalls to thereby deform the resilient band out of locking engagement with the cannula housing.

16. An infusion set according to claim 15, and further comprising a groove formed in the upper surface of the cannula housing, the groove being sized to receive the resilient band.

17. An infusion set according to claim 16, and further comprising a locking protrusion formed on an upper surface of the cannula housing adjacent the groove for engaging the resilient band.

18. An infusion set according to claim 15, wherein the sidewalls taper toward the resilient band.

19. An infusion set according to claim 14, and further comprising:

a ferrule mounted in the cannula housing such that a cannula can be connected to a forward end of the ferrule; and a septum connected at a rearward end of the ferrule to seal the ferrule against ingress and egress of fluid when the housings are disconnected, the hollow needle extending through the septum and into the ferrule when the housings are connected.

20. An infusion set according to claim 19, and further comprising at least one alignment groove formed on one of the housings and at least one guide rail formed on the other housing, the alignment groove and guide rail being engageable during sliding movement of the housings to thereby center the hollow needle relative to the septum and ferrule during connection of the housings.

21. An infusion set according to claim 19, wherein a barb is formed on the forward end of the ferrule for connection to the connection end of a cannula in sealing engagement with the barb.

22. An infusion set according to claim 21, wherein the cannula housing includes a bore through which the cannula extends.

23. An infusion set according to claim 21, wherein the septum is constructed of a resilient material that biases the connection end of the cannula into sealing engagement with an edge of the bore.

24. An infusion set according to claim 19, and further comprising a septum retainer mounted between the cannula housing and the septum.

* * * * *